(12) United States Patent
Ruellan et al.

(10) Patent No.: US 9,746,384 B2
(45) Date of Patent: Aug. 29, 2017

(54) HEAT FLUX SENSOR WITH INCREASED RESOLUTION

(71) Applicant: COMMISSARIAT A L'ENERGIE ATOMIQUE ET AUX ENE ALT, Paris (FR)

(72) Inventors: Jeremie Ruellan, Grenoble (FR); Laurent Duraffourg, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 732 days.

(21) Appl. No.: 14/029,920

(22) Filed: Sep. 18, 2013

(65) Prior Publication Data

US 2014/0079091 A1 Mar. 20, 2014

(30) Foreign Application Priority Data

Sep. 19, 2012 (FR) ..................................... 12 58798

(51) Int. Cl.
*G01N 25/18* (2006.01)
*G01K 17/06* (2006.01)
*G01N 27/18* (2006.01)
*G01N 30/66* (2006.01)

(52) U.S. Cl.
CPC ............. *G01K 17/06* (2013.01); *G01N 27/18* (2013.01); *G01N 30/66* (2013.01)

(58) Field of Classification Search
USPC ........................ 73/23.4, 25.04, 25.05; 374/29
See application file for complete search history.

(56) References Cited

U.S. PATENT DOCUMENTS

| | | | |
|---|---|---|---|
| 4,902,138 A | 2/1990 | Goeldner et al. | |
| 7,963,147 B2 * | 6/2011 | Jun ...................... | G01N 27/128 73/25.01 |
| 2004/0195096 A1 | 10/2004 | Tsamis et al. | |
| 2007/0222011 A1 | 9/2007 | Robert et al. | |
| 2008/0314148 A1 | 12/2008 | Robert | |

FOREIGN PATENT DOCUMENTS

| | | |
|---|---|---|
| CN | 88 1 01718 A | 10/1988 |
| CN | 1538934 A | 10/2004 |
| CN | 101795505 A | 8/2010 |
| CN | 102288644 A | 12/2011 |

(Continued)

OTHER PUBLICATIONS

U.S. Appl. No. 14/619,656, filed Feb. 11, 2015, Ruellan, et al.
(Continued)

*Primary Examiner* — Lisa Caputo
*Assistant Examiner* — Nasir U Ahmed
(74) *Attorney, Agent, or Firm* — Oblon, McClelland, Maier & Neustadt, L.L.P.

(57) ABSTRACT

A heat flux sensor comprising at least one support, where at least one membrane is suspended relative to the support by at least four nanowires, where the membrane is made from at least one current-conducting material, and where the nanowires are made from a current-conducting material, with two nanowires connected to a current source to polarize the membrane between two terminals and a heater for heating the membrane, and where two nanowires are connected to a voltmeter to form measure the voltage at the terminals of the membrane.

20 Claims, 5 Drawing Sheets

(56) References Cited

FOREIGN PATENT DOCUMENTS

Figure 1:
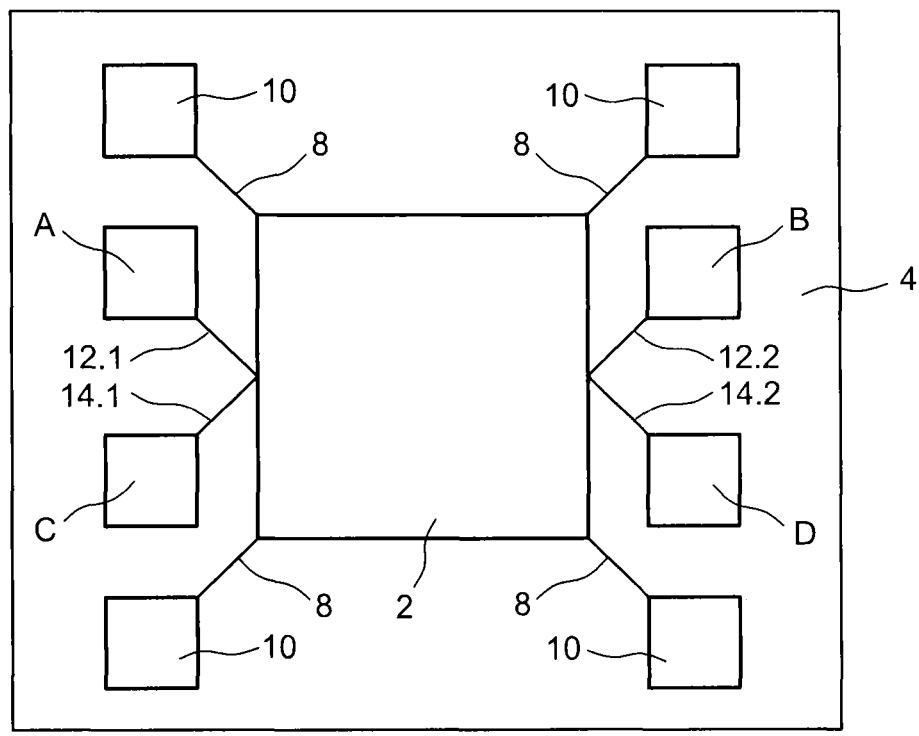

| CN | 102359980 A | 2/2012 |
|---|---|---|
| CN | 102549422 A | 7/2012 |
| EP | 1 840 582 A1 | 10/2007 |
| FR | 2 917 731 A1 | 12/2008 |
| WO | 2011/044547 A2 | 4/2011 |
| WO | WO 2011/154363 A2 | 12/2011 |

OTHER PUBLICATIONS

French Preliminary Search Report issued Jan. 10, 2013, in Patent Application No. FR 1258798, filed Sep. 19, 2012 (With English Translation of Category of Cited Documents).
F. T. Zhang, et al., "A micro-Pirani vacuum gauge based on micro-hotplate technology", Sensors and Actuators A, vol. 126, No. 2, XP 027935467, Feb. 14, 2006, pp. 300-305.
Fred Klaessig, et al., "Current Perspectives in Nanotechnology Terminology and Nomenclature", Nanotechnology Standards, XP 055047000, Jan. 2011, pp. 21-52.
F. Rastrello, et al., "Thermal conductivity detector compact Spice model based on experimental measurements and 3D simulations", Sensors and Actuators A: Physical, vol. 178, XP 055047308, May 2012, pp. 49-56.
U.S. Appl. No. 14/030,205, filed Sep. 18, 2013, Duraffourg et al.
Search Report issued Oct. 9, 2013, in European Patent Application No. 13184581.0 (with English Translation of Category of Cited Documents).
I. Bargatin, et al., "Efficient electrothermal actuation of multiple modes of high-frequency nanoelectromechanical resonators", Applied Physics Letters, vol. 90, 2007, pp. 093116-1-093116-3.
Bradley C. Kaanta, et al., "A monolithically fabricated gas chromatography separation column with an integrated high sensitivity thermal conductivity detector", Journal of Micromechanics and Microengineering, vol. 20, 2010, 6 pages.
Behzad Razavi, "A Study of Phase Noise in CMOS Oscillators", IEEE Journal of Solid-State Circuits, vol. 31, No. 3, Mar. 1996, pp. 331-343.
E Mile, et al., "In-plane nanoelectromechanical resonators based on silicon nanowire piezoresistive detection", Nanotechnology, vol. 21, 2010, 7 pages.
J. F. Creemer, et al., "MEMS Hotplates with TiN as a Heater Material", IEEE $4^{th}$ Conference on Sensors, 2005, pp. 330-333.
J. F. Creemer, et al., "Microhotplates with TiN heaters", Sensors and Actuators A, vol. 148, 2008, pp. 416-421.
K. Khosraviani, et al., "Low-Cost Surface Micromachined Pirani Pressure Sensor with Atmospheric pressure Range", Electrical and Computer Engineering, CCECE Canadian Conference, 2007, pp. 153-156.
R. Puers, et al., "The NanoPirani—an extremely miniaturized pressure sensor fabricated by focused ion beam rapid prototyping", Sensors and Actuators A, vol. 97-98, 2002, pp. 208-214.
Combined Office Action and Search Report issued Feb. 28, 2017 in Chinese Patent Application No. 201310436123.5 (with English translation of Office Action and English translation of categories of cited documents).

* cited by examiner

HEAT FLUX SENSOR WITH INCREASED RESOLUTION

TECHNICAL FIELD AND PRIOR ART

The present invention relates to a heat flux sensor, and to a system for determining the concentration of the components of a gas from its thermal and fluid characteristics, comprising at least one such sensor.

A heat flux sensor is understood to mean any sensor measuring a heat exchange between the body of the sensor, for example a membrane, and the fluid medium in which the sensor is positioned. This heat flux sensor is, for example, a gas sensor, in particular of the TCD type (Thermal Conductivity Detector), or a pressure sensor, notably of the Pirani gauge type.

This type of sensor may be positioned at the outlet of a chromatography column, more specifically a chromatography microcolumn, where the latter enables the different gaseous elements of a complex blend to be separated chronologically. The sensor is used to quantify the relative concentration of the analytes of the gas to be analysed which arrive in succession at its surface. The analytes are blended in a gas, called the carrier gas, which is sent into the chromatography column and to the sensor at a fixed speed.

The carrier gas may be dry air or an inert gas, for example.

Several types of sensor exist which can be positioned at the outlet of a chromatography column.

Flame ionisation detectors (FIDs).

The gases to be analysed are burnt in a hydrogen stream, creating ions and electrons. The charged particles are collected by electrodes, and the generated current is measured with a picoammeter. Firstly, this sensor allows detection only of organic components. Secondly, it requires a hydrogen stream, and the quantity of ions produced is always small. Finally, the size of the sensor cannot be reduced.

Gravimetric sensors also exist. The aim in this case is to measure the quantity of mass of the target gas adsorbed at the surface of the sensor.

The sensor is generally a system which vibrates at an natural oscillation frequency. The technique consists in measuring the frequency shift due to the gravimetric effect in the low frequencies caused by adsorption of the gas. These sensors are ultra-sensitive for large gaseous molecules, but are less sensitive in terms of measurement of concentration for very light and/or volatile molecules.

Optical sensors also exist, the operating principle of which is generally based on infrared absorption of an optical flow. The sensors are appropriate for detecting carbonised elements. But in order to be able to detect other types of gas the number of laser sources must be increased, which would greatly increase the complexity and cost of such a device. These sensors are also difficult to miniaturise.

Electronic sensors, the detection principle of which is based on the variation of an electrical property (electrical resistance, resistance, surface potential) caused by the presence of gas molecules at its surface. These sensors require surface functionalisation. Macroscopic sensors are relatively insensitive. Sensors of micrometric or nanometric size, for their part, suffer from problems of drift, i.e. chronological drift of the signal independent of the phenomenon to be measured, and from extreme sensitivity to the initial surface states. They must also be functionalised.

Finally, Thermal Conductivity Detectors, TCDs, exist.

A TCD detector may comprise a wire heated to a high temperature, the electrical resistance of which is measured. The wire has a given temperature for a given gas. When the gas changes, the properties of the thermal environment (thermal conductance, viscosity, thermal convection) change, which causes the temperature of the wire to vary. This variation itself causes a change of electrical resistance which is detected through a measuring bridge. The higher the temperature of the TCD sensor, the better its resolution. The sensor is able to operate in air, but the use of an oxygen-free environment means that the temperature limit imposed by a possible combustion of the wire ceases to apply. The TCD wire must generally be placed in a helium or hydrogen carrier gas stream. This represents a major limitation of the detector. In addition there is a great contrast of the thermal constants between these light gases and the analytes to be detected, which makes the system more sensitive than in a simple dry air stream.

Document WO2001/044547 describes a TCD sensor intended to be positioned at the outlet of a chromatography column. This TCD sensor comprises a lengthened support plate, a lengthened heating element positioned on the support plate, where the support plate and the heating element are suspended in a chamber in which a gas flows. Two contacts are installed to power the heating element, and two contacts to measure the voltage. The heating element is shaped like a battlement. The electrical resistance of the heating element is measured and enables the composition of the gas in contact with the support plate to be determined.

This sensor is complex to produce since it requires that the bracket is manufactured, and then that the heating element and the electrical connections between the heating element and the substrate are produced.

In addition it is relatively bulky.

DESCRIPTION OF THE INVENTION

It is consequently one aim of the present invention to provide a heat flux sensor with improved resolution, which is simple to produce and which occupies a small volume.

The declared aim is achieved by a heat flux sensor comprising at least one membrane suspended relative to a substrate by nanowires, where means of heating and polarising the membrane formed by nanowires connect the membrane to at least one current source, and means of measuring the electrical voltage at the membrane's terminals.

The voltage measuring means may be formed by nanowires connecting the membrane and a voltmeter.

Use of nanowires between the membrane and the substrate provides thermal insulation of the membrane relative to the substrate, which limits the heat leakages via the membrane's suspension means, and makes the device more sensitive to the heat leakages occurring due to the gas.

The heating nanowires and the polarisation nanowires and nanowires for measuring the voltage variation may form the mechanical suspension nanowires, which reduces still further the heat leakage areas.

The heating nanowires are also advantageously used for polarisation, and the number of nanowires is therefore smaller.

The polarisation nanowires and the nanowires for measuring the voltage variation are preferentially separate, which allows a highly resolved measurement of the temperature of the membrane.

The heat flux sensor has very small dimensions; it may then be co-integrated with the electronics and the pre-analytic system formed by the chromatography column.

This sensor has the advantage that it provides a very large heat exchange surface with the gas, which makes the sensor more sensitive to the nature of the gas.

One subject-matter of the present invention is then a heat flux sensor comprising at least one first support, where at least one first membrane is suspended relative to the support by at least four nanowires, where said first membrane is made from at least one current-conducting material, and where the nanowires are made from a current-conducting material, with two nanowires connected to a current source to form means of polarisation between two terminals of the first membrane and means of heating said first membrane, and where two nanowires are connected to means for measuring the voltage at the terminals of the first membrane.

Voltage measuring means may be produced by all known means for voltage measurement and, for example, a voltmeter, an oscilloscope or again a synchronous detection device.

The nanowires advantageously have a section of between $10 \times 10$ nm$^2$ and $1000 \times 1000$ nm$^2$ Also advantageously, the first membrane is between 10 nm and 1 µm thick.

In one example embodiment the first membrane and the nanowires are formed by the same layer of current-conducting material such that they form a single part.

The first membrane and the nanowires may be made of a semiconductor material, for example of N- or P-doped silicon, germanium or SiGe. The nanowires are made for example of doped silicon such that the thermal resistivity coefficient is cancelled.

As a variant, the first membrane and the nanowires may be made of any conductive material, and preferably of a conductive material with a high temperature coefficient of resistance, TCR, such as the semiconductor materials, TiN, the metal alloys and the silicides.

The first membrane comprises, for example, a first portion forming a single part with the nanowires, and a second portion formed by a layer of material formed on the first portion, where the material of the nanowires and the first portion have low thermal conductivity, and the material of the second portion has a high temperature coefficient of resistance.

The thermal conductivity of the material of the nanowires and of the first portion is preferably less than 100 W/m·K, and the temperature coefficient of resistance of the material of the second portion is preferably greater than 1000 ppm/K.

The nanowires and the first portion are made, for example, of silicon, and the second portion is made of TiN.

The second portion may be made from any conductive material with a high temperature coefficient of resistance (TCR), such as the semiconductor materials, TiN, the metal alloys, and the silicides. More generally, this material is chosen such that it has thermal conductivity, electrical conductivity and a temperature coefficient of resistance which are as high as possible, while the material of the first portion is chosen to have the lowest possible thermal conductivity.

The current source may be an alternating current source, which may have a frequency of between 10 Hz and 1 MHz, and advantageously between 1 KHz and 10 KHz.

The sensor may comprise additional suspension elements, configured solely for the mechanical suspension of the first membrane relative to the support. These suspension elements may be non-linear, for example they may be coiled or equipped with two rectilinear portions connected by a rectangular frame.

The heat flux sensor may also comprise embedments of the nanowires and/or of the additional means of suspension on the support, where the embedments of the nanowires and/or of the additional means of suspension are nanostructured so as to reduce the thermal conduction of the embedments.

In an advantageous example the first membrane is rhomb-shaped, the nanowires being connected to the apexes linked by the larger diagonal of the rhomb.

The heat flux sensor may comprise a second membrane suspended from a second support by at least four nanowires, where said second membrane is positioned parallel to the first membrane at a non-zero distance, where said nanowires are made from a current-conducting material, and where two nanowires are connected to a second current source to form polarisation means between two terminals of the second membrane, and where two nanowires are connected from the voltage measurement means to the terminals of the second membrane.

According to one variant, the first and second current sources are alternating current sources, and the second current source delivers a current of a frequency different to the frequency of the current delivered by the first current source.

According to another variant, the first and second current sources are direct current sources, and the second current source delivers a current which is lower than the current delivered by the first current source, so as to prevent self-heating in the second membrane.

Another subject-matter of the present invention is a system for determining the concentration of a gaseous environment comprising at least one heat flux sensor according to the present invention, and an electronic unit for processing the electrical voltage values delivered by the sensor.

Another subject-matter of the present invention is a device for analysing a gas or a blend of gases comprising a gas chromatography column, and at least one determination system according to the present invention, where the membrane is suspended in a channel connected to the outlet of the gas chromatography column.

BRIEF DESCRIPTION OF THE ILLUSTRATIONS

Figure 2:
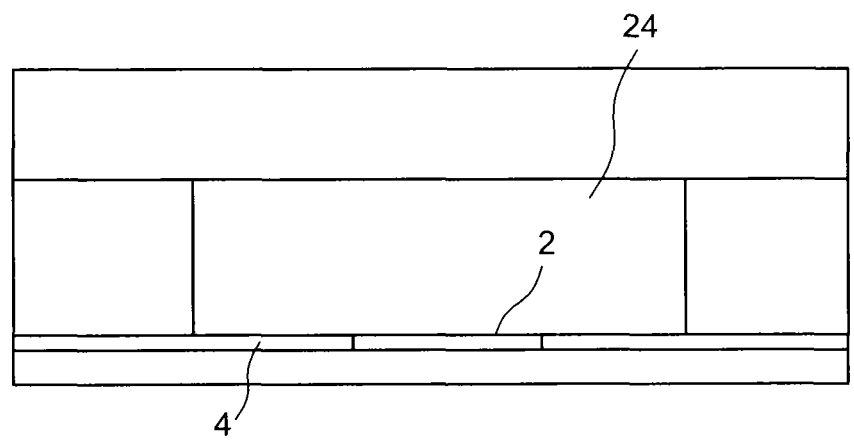
Figure 3:
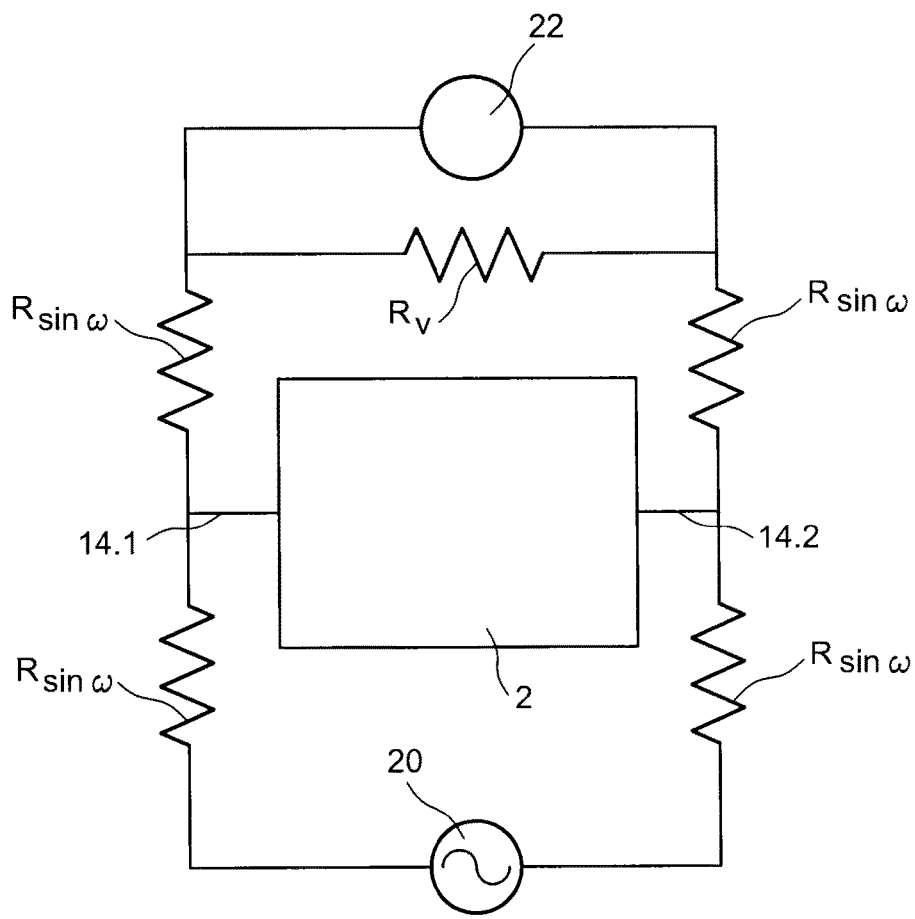
Figure 4:
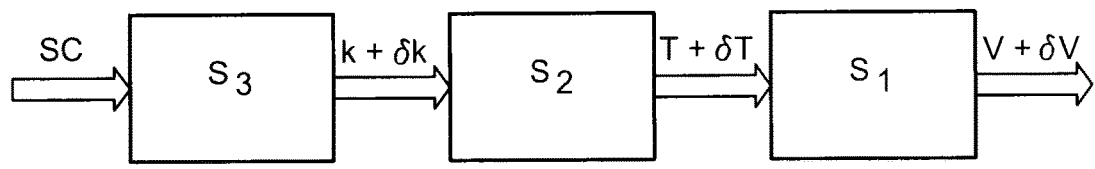
Figure 5:
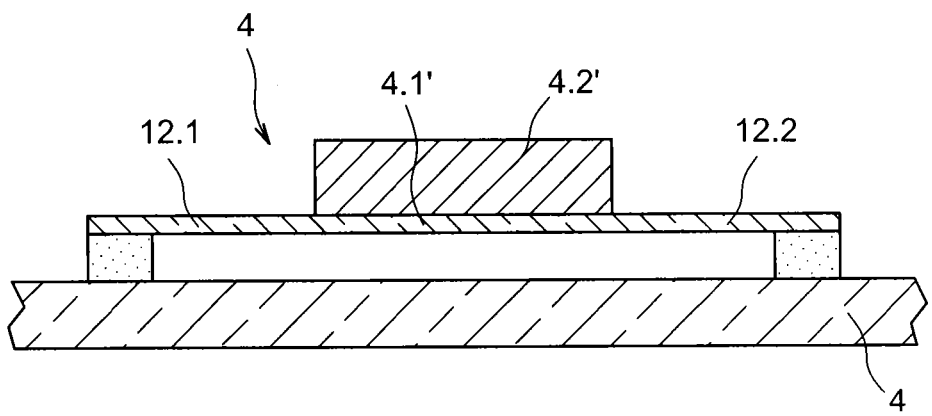
Figure 6A:
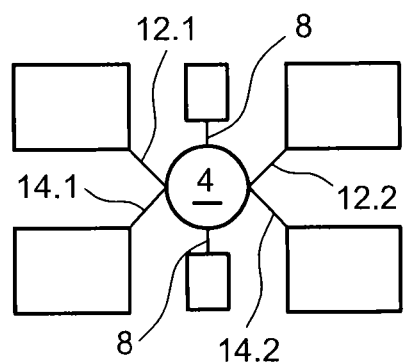
Figure 6B:
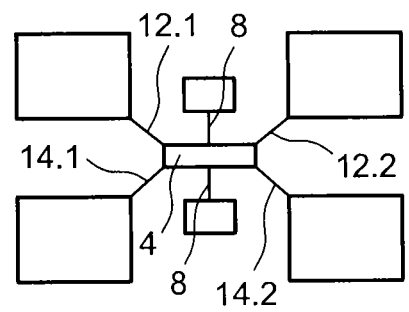
Figure 6C:
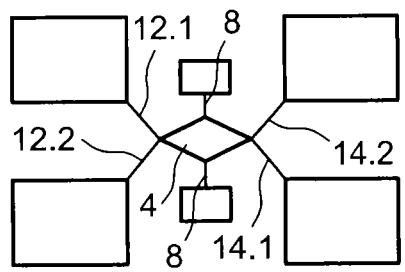
Figure 6D:
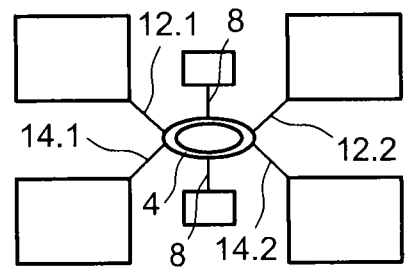
Figure 7:
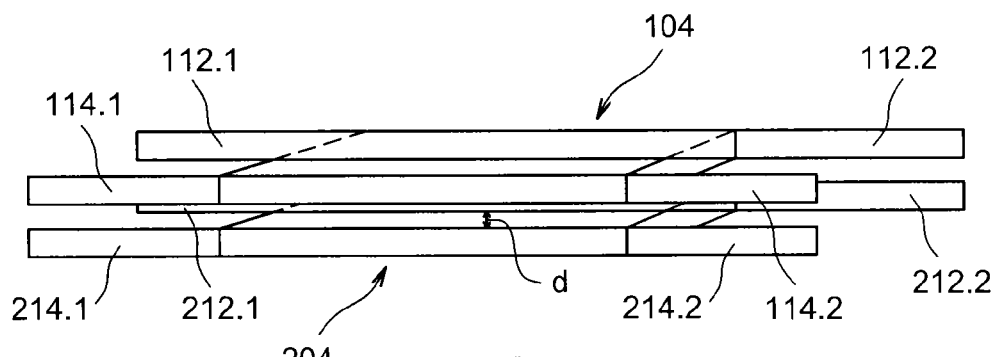

The present invention will be better understood using the description which follows and the appended illustrations, in which:

FIG. 1 is a schematic representation of a top view of an example embodiment of a portion of a heat flux sensor according to the invention FIG. 2 is a transverse section view of a heat flux sensor according to the invention; the section also represents an example of a fluid channel in which the sensor may be incorporated, FIG. 3 is a schematic representation of the electrical circuit for polarising the membrane and for measuring the voltage at the terminals of the membrane, FIG. 4 is a flow diagram representing the successive stages of the operation of a heat flux sensor in the special case of a gas sensor according to the present invention, FIG. 5 is a schematic representation of a side view of another example embodiment of a heat flux sensor in the present invention, FIGS. 6A to 6D are schematic representations of variant embodiments of a heat flux sensor according to the present invention, FIG. 7 is a perspective representation of another example embodiment of a heat flux sensor according to the present invention allowing differential measurement, FIGS. 8A to 8H are schematic representations of the different steps of an example of a method of production of a heat flux sensor according to the present invention,

DETAILED DESCRIPTION OF PARTICULAR EMBODIMENTS

In the present application the expression "heat flux sensor" is understood to mean the device sensing a temperature variation and producing an electrical signal representative of the variation of electrical voltage, and the expression "system for determining concentration" is understood to mean a system comprising the heat flux sensor and means for processing the signals transmitted by the sensor and delivering an analyte concentration value.

In the following description the terms "gas", "gaseous blend" and "gaseous environment" are considered to be synonyms, and designate an analyte or blend of analytes to be analysed.

In FIG. 1 a sensor may be seen according to an example embodiment comprising a membrane 2 suspended relative to a substrate 4 by suspension means. The suspension means are formed by nanowires 8 connecting membrane 2 to anchoring studs 10 of the substrate.

The heat flux sensor also comprises electrical connections 12.1, 12.2 and 14.1, 14.2 formed by nanowires connecting the membrane to electrical contact pads A, B, C, D respectively.

Very advantageously, nanowires 12.1, 12.2 form both means of polarising the membrane and means of heating membrane 2. The nanowires are connected electrically to a current source 20 (represented in FIG. 3). The number of connections between the substrate and the membrane which may be the source of heat leakages is thus small.

Nanowires 14.1, 14.2 are connected electrically to a voltmeter 22 (represented in FIG. 3), and thus form means of measuring the variation of the voltage at the terminals of the membrane.

In FIG. 2 a section view may be seen of the sensor positioned in a fluid channel 24 connected to a source of supply of a gas to be analysed.

In the present application the expression "nanowire" is understood to mean electrically conductive wires of nanometric size, i.e. the section of which is between 10×10 nm² and 1000×1000 nm², and is advantageously equal to 50×50 nm², and the length of which is between 100 nm and 10 μm, and advantageously of the order of 2 μm.

The membrane preferably has an area of between: 1 μm² and 100×100 μm², and is between 10 nm and 1 μm thick.

The material is chosen such that it has a high Thermal Coefficient of Resistivity (TCR). In addition, it is preferably chosen such that it has a very high melting point, thus allowing high operating temperatures, increasing the signal-to-noise ratio.

The suspended portion of the sensor may be made of silicon. It may be preferably made from a doped material, to increase the Thermal Coefficient of Resistivity. For example, the suspended portion of the sensor may be made of N- or P-doped silicon. The silicon may advantageously be porous so as to increase the heat exchange surface.

Advantageously it may be made of germanium or SiGe.

In the case of a structure made of silicon the operating temperature is of the order of 600° C.

In a particularly advantageous manner, the membrane and the nanowires may be made of TiN, permitting operating temperatures of the order of 2000° C., which enables the signal-to-noise ratio to be increased.

In the case of silicon the TCR is of the order of 1000 ppm, and in the case of TiN the TCR is of the order of 100 ppm.

In FIG. 3 a diagram of an electrical circuit of the sensor according to the invention is represented.

Current source 20 is connected to contacts A and B, and voltmeter 22 is connected to contacts C and D. The sensor uses a purely resistive transduction method, where the temperature variations in the membrane are measured by means of variations of its electrical resistivity.

$R_V$ designates the impedance of the voltmeter, and $R_{sin\ w}$ designates the electrical resistance of each of nanowires 12.1, 12.2, 14.1, 14.2.

$V_1$-$V_2$ is the voltage measured at the terminals of membrane 4.

The voltmeter preferably has a high impedance compared to the resistances $R_{sin\ w}$ of nanowires 14.1, 14.2. In this manner, the voltage at the terminals of nanowires 14.1, 14.1 may be disregarded. The voltage measured at points C and D may then be considered to be equal to $V_1$-$V_2$.

In addition, this enables the noise phenomena which may occur in the nanowires to be disregarded.

The sensor delivers a signal representing the variation of the voltage at the terminals of the membrane; from this measurement the variation of an electrical resistance of the membrane is determined, due to the variation of the temperature of the membrane which, itself, depends on the composition of the gaseous environment in contact with the membrane. It is then possible to determine the composition of the gaseous environment.

We shall show the interest of the sensor according to the present invention.

The membrane is heated by a Joule effect.

A current flows between points A and B, i.e. in nanowire 12.1, in membrane 2 and in nanowire 12.2, and heats the assembly by the Joule effect.

And nanowires 12.1, 12.2 have a much smaller section than that of the membrane; it is therefore considered that all the power generated originates from the nanowires. The membrane is therefore principally heated by conduction through the nanowires, and the thermal power is produced by the nanowires.

The structure is polarised using a current flowing between contacts A and B. The thermal power produced in the nanowires is equal to $$P_J = 2R_{sin\ w}I^2$$

The thermal losses of membrane 2 may be represented by two resistances:

$R_{th_{sin\ w}}$: the heat resistance of each nanowire; this resistance is preferably maximised in order to limit the heat losses through the nanowires.

$R_{th_{gaz}}$: the heat resistance of the gas; this resistance is preferably low, to facilitate heat exchanges with the membrane.

The rise in temperature in the membrane is then written as follows:

$$\Delta T = \frac{P_j}{G_{th_{sinw}} + G_{th_{gaz}}}$$

-continued

Where $G_{th_{sinw}} = \frac{1}{R_{th_{sinw}}}$ and $G_{th_{gaz}} = \frac{1}{R_{th_{gaz}}}$ are the thermal conductances of the nanowire and of the gas.

The temperature variation may be written:

$$\Delta T = \frac{P_j}{G_{th_{gaz}}\left(1 + \frac{GG_{th_{sinw}}}{G_{th_{gaz}}}\right)} \quad (1)$$

The thermal conductivity of the gas may be written:

$$G_{th_{gaz}} = \frac{k_{th_{gaz}} L_m^2}{d_t}$$

where $L_m$ is the characteristic length of the membrane, $d_t$ is the distance between the thermostat and the membrane, and $k_{th_{gaz}}$ is the thermal conductivity of the gas.

By virtue of the invention, membrane 4 is thermally isolated from the substrate by the nanowires, which have the advantage that they have a higher thermal resistivity than that of the membrane, in particular due to the confinement of the phonons in the nanometric structures. The thermal conductivity of the nanowires is therefore low.

As a consequence ratio $$\frac{G_{th_{gaz}}}{G_{th_{sinw}}}$$

is high.

From relationship (I) it is deduced that temperature variation $\Delta T$ may be approximated at $$\Delta T = \frac{P_j}{G_{th_{gaz}}} \text{ or } \Delta T = \frac{P_j}{\frac{k_{th_{gaz}} L_m^2}{d_t}}$$

By increasing ratio $$\frac{G_{th_{gaz}}}{G_{th_{sinw}}},$$

the dependence of the temperature relative to the thermal conductivity of the gas is increased.

Temperature variation $\Delta T$ is then inversely proportional to the thermal conductivity of the gas. The sensor according to the invention is therefore very sensitive to the nature of the gas coming into contact with the membrane.

The temperature variation is written:

$$\Delta T = \frac{P_j}{G_{th_{sinw}} \frac{k_{th_{gaz}} L_m^2}{d_t}} +$$

We shall determine the sensitivity of the sensor according to the present invention.

In FIG. 4 a block diagram is seen representing the successive steps of the method of determination leading to the detection of a gas.

$\delta C$ represents an analyte concentration peak, k the thermal conductivity of the gaseous environment surrounding the membrane;

T the temperature of the membrane,

V the voltage at the terminals of the membrane which is comparable to the voltage at the terminals of the voltmeter, $S_1$, $S_2$ and $S_3$ represent the sensitivities of each of the steps of determination.

When an analyte concentration peak $\delta C$ arrives at the surface of the membrane this produces a variation of the thermal conductivity of the gas $\delta k$. We then define the sensitivity of this step by $$S_3 = \frac{\delta k}{\delta C}.$$

The temperature of the membrane is dependent on the thermal conductivity of the gas. We then define $$S_2 = \frac{\delta T}{\delta k}.$$

A temperature variation leads to a variation of the electrical resistance of the membrane, and consequently a variation of the voltage at its terminals.

We define $$S_1 = \frac{1}{V}\frac{\delta V}{\delta T}.$$

S1 is the temperature coefficient of resistance of the material.

A change of analyte concentration thus causes a change of voltage at the terminals of the membrane.

In the general case of a heat flux sensor, the step of detection of an analyte concentration peak $\delta C$, which creates the relationship between the analyte concentration and the thermal conductivity, does not take place The total sensitivity of the system is written:

$$S_{tot} = \frac{1}{V}\frac{\delta V}{\delta C} = S_1 S_2 S_3$$

We shall now determine the sensor's resolution.

The sensor's resolution is limited by its noise.

Several noise sources must be taken into account:

Johnson noise: $S_J = 4k_b TR$, related to the variations of the mobility of the carriers (phonons/electrons and phonons/holes interactions).

The flicker noise:

$$S_{1/f} = \frac{HV^2}{Nf}$$

The thermal noise or phonon noise:

$$S_{phonons} = \frac{4kT^2}{G},$$

relating to the fluctuations of the internal energy of the membrane.

The voltage resolution limit of the system is then given by the integral of the total noise for the bandwidth:

$$\delta V \cong \sqrt{(S_j + S_{1/f} + S_{phonons}) \cdot BW}$$

BW is the signal's integration bandwidth.

The concentration resolution of the system may then be deduced:

$$\delta C = \frac{1}{V \cdot S_{tot}} \sqrt{(S_j + S_{1/f} + S_{phonons}) \cdot BW}$$

To reduce the flicker noise, also called the "1/f noise", it is advantageous to make the measurements dynamically, i.e. working with an alternating current source at a sufficiently high frequency.

The value of the frequency of the supply current is chosen in order for the system to operate in quasi-static mode. Indeed, if the current frequency is too high the inertia of the system does not allow a substantial rise of the membrane, and the amplitude of the wanted signal is reduced.

Furthermore, the fact of modulating the temperature rise may enable the static drifts of the electrical signal or of the temperature to be disregarded.

This measurement is made, for example, by imposing an alternating current and by measuring the harmonics at 2ω of the voltage at the terminals of the membrane. The current imposed at ω causes a variation of the temperature, and therefore of the resistance in the wire at 2ω, which may be written ΔR=ΔR0×cos(2ωt). By injecting a constant current in wire I0, this therefore leads to a component of the voltage which is equal to ΔR*I0.

The membrane and the nanowires may be made from different materials. By choosing the materials the influence of the phenomena occurring in the nanowires or their anchors may be limited, in order that temperature variations appear only in the membrane, which enables the sensitivity of the sensor to be increased.

In an advantageous example embodiment represented in FIG. 5, the sensor comprises a portion in a single piece made of silicon forming the nanowires and a first portion of membrane 4.1' forming a support and a second portion 4.2' of membrane 4' covering first portion 4.1' and forming the sensitive portion of the sensor, where second portion 4.2' is made from a material having a high temperature coefficient of resistance.

In an advantageous example, second portion 4.2' is made of TiN, which has a high temperature coefficient of resistance and a very high melting point, of over 2900° C.

In this example embodiment second portion 4.2' of membrane 4' is heated by nanowires 12.1, 12.2 and first portion 4.1'.

Temperature coefficient of resistance characterises the influence of temperature on the material's electrical resistance.

The system's output signal is therefore proportional to the temperature coefficient of resistance, and the system's minimum resolution is inversely proportional to this coefficient.

By choosing a material with a high temperature coefficient of resistance minimal resolution may be lowered further.

In an even more advantageous manner, the nanowires are made of a material having a very low or near-zero temperature coefficient of resistance; the electrical resistance of the nanowires is then almost insensitive to temperature, and only the resistance of the membrane varies according to the temperature. In this example the first portion of the membrane is, due to the manufacturing method, also made of a material having a very low temperature coefficient of resistance; however, due to the deposition of the layer of material having a high temperature coefficient of resistance, the membrane's electrical resistance varies greatly with temperature. The nanowires are made for example of doped silicon such that the thermal resistivity coefficient is cancelled.

In FIGS. 6A to 6D other example architectures of a sensor according to the invention may be seen.

In FIG. 6A membrane 4 has the shape of a disk and is suspended mechanically by two nanowires.

In FIG. 6B membrane 4 has the shape of a rectangle and is suspended mechanically by two nanowires 8 which are connected to the membrane in the middles of the larger sides of the rectangle. Electrical connection nanowires 12.1, 12.2, 14.1, 14.2 are connected to the four apexes of the rectangle.

In FIG. 6C membrane 4 has the shape of a rhomb and is suspended mechanically by two nanowires at the two opposing apexes of the rhomb.

Electrical connection nanowires 12.1, 12.2, 14.1, 14.2 are connected in pairs to each of the other two opposing apexes of the rhomb linked by the diagonal of greater length.

In FIG. 6D membrane 4 has the shape of an elliptical ring and is suspended mechanically by two nanowires 8 aligned with the small axis of the ellipse. Electrical connection nanowires 12.1, 12.2, 14.1, 14.2 are connected in pairs to the two ends of the ellipse aligned with the large axis.

The structure of FIG. 6B is particularly advantageous since it provides near-uniform and fast diffusion of the temperature through the membrane. The structure of FIG. 6C provides near-uniform and relatively fast diffusion through the membrane.

As was explained with the example of FIG. 1, the mechanically suspended nanowires may be omitted.

In FIG. 7 an example embodiment may be seen of a heat flux sensor comprising a first and the second membrane, which are suspended and positioned parallel with one another.

First membrane 104 is intended to excite the sensor and second membrane 204 is intended for detection.

The first membrane is suspended by four nanowires 112.1, 112.2, 114.1, 114.2. Nanowires 112.1, 112.2 are intended to be connected to a first current source to heat first membrane 104.

The voltage of the first membrane is preferably measured and its temperature is determined. Nanowires 112.1, 112.2 advantageously polarise the first membrane, and nanowires 114.1, 114.2 are connected to a voltmeter.

As a variant it might be envisaged not to determine the temperature of the first membrane; in this case nanowires 114.1, 114.2 act solely as suspension means.

Second membrane 204 is also suspended by four nanowires 212.1, 212.2, 214.1, 214.1.

The first and second membranes are separated by a distance d, for example of the order of one to several hundred nanometers.

Nanowires 212.1, 212.2 are intended to be connected to a second current source to polarise the membrane. The voltage source preferably delivers a constant current of low amplitude compared to the current delivered by the first current source, in order to prevent any interference between the excitation signal and the detection signal. By polarising with a current of low amplitude, substantial heating of the second membrane by the current used to polarise the membrane is prevented.

Nanowires 214.1, 214.2 are intended to be connected to a voltmeter to measure the voltage variation in the membrane resulting from the heating of the second membrane.

The operation of this sensor will now be described.

The gaseous environment to be analysed is located between the two membranes 104, 204.

A current flows in nanowires 112.1, 112.2 and in first membrane 104. By the Joule effect, nanowires 112.1, 112.2 are heated and heat first membrane 104 by conduction. The second membrane is heated by conduction through the gas located between the two membranes.

The heating of the second membrane therefore depends on the thermal conductivity of the gas.

The voltage is measured at the terminals of second membrane 204 by means of the voltmeter.

From this measurement the temperature of the second membrane is determined. Knowing the temperature of the first membrane, it is then possible to deduce the composition of the gaseous environment located between the two membranes which caused the heating of the second membrane from the heating of the first membrane, in a similar manner to the method described above for the sensor with one membrane.

As was described above, the excitation signal may be an alternating current, which enables the flicker noise to be reduced. In this case the current polarising the second membrane is a direct current.

The shape of the membranes is not restrictive, and the shapes of the example embodiments of FIGS. 6A to 6D may be used in the sensor of FIG. 7.

It is also conceivable to place one or more nanowires facing a membrane, which recovers the heat created by the nanowires.

In addition, the embedments of the means of mechanical suspension of the membrane and of the nanowires for heating the membrane may advantageously be nano-structured in order to limit the thermal conduction by the anchors. Indeed, by making, for example, holes of nanometric size, for example in silicon, of the order of 20 nm in diameter with a pitch of 15 nm to 20 nm, diffusion of the heat may be blocked, whilst the satisfactory electrical conduction properties are retained. The embedments of the suspensions thus become thermally insulating, but remain conductors for the electrons (or the holes). As an example, a nano-structured monocrystalline silicon of this kind exhibits thermal conductivity values which are as low as those of amorphous silicon. These insulating means are called phononic insulators.

It may be conceived to fill the holes with an insulating material such as SiO2 or SiOC, or SiN, which may be advantageous to strengthen the anchors mechanically.

We shall now describe an example method of manufacture of the sensor according to the present invention.

In FIGS. 8A to 8H schematic representations of different steps of the production method may be seen.

Figure 8A:
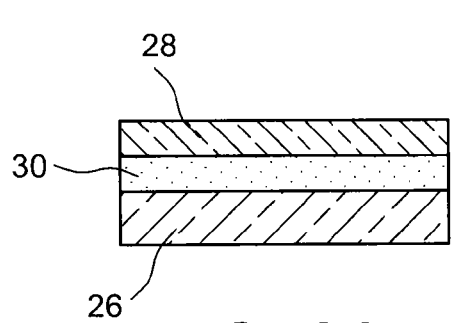

In the described example, a plate of SOI (Silicon On Insulator) is used, represented in FIG. 8A. The SOI substrate comprises a layer of silicon 26 and a layer of monocrystalline silicon 28, where layers 26 and 28 are separated by a layer of $SiO_2$ 30. Layer of monocrystalline silicon 28 forms the front face.

Figure 8B:
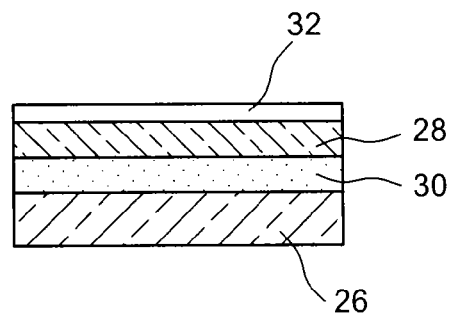

In a first step a layer of oxide $SiO_2$ 32 is deposited on layer 28. The element formed in this manner is represented in FIG. 8B.

In a subsequent step, a P++ doping is applied, for example using boron, to silicon layer 28 located between oxide layer 30 and oxide layer 32.

Doping through the oxide layer allows more uniform distribution of the dopants in layer 28. The doping obtained is of the order of $1 \cdot 10^{19}$ at./cm$^3$). The effect of this doping is to maximise the temperature coefficient of resistance of the silicon.

Figure 8C:
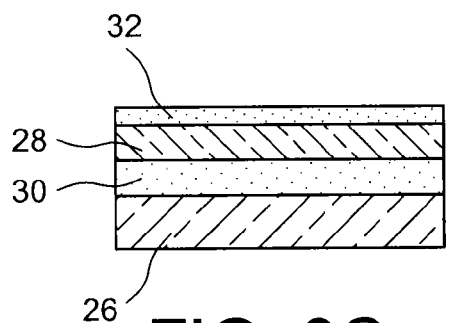

The element formed in this manner is represented in FIG. 8C. The doping is represented symbolically by points.

In a subsequent step oxide layer 32 is removed and a resin layer 33 is deposited, in which the contours of the patterns in resin 32 are defined by lithography, for example by Deep-UV (DUV) lithography, or by hybrid DUV and e-beam lithography. These lithography methods are well known to those skilled in the art and will not be described in detail. E-beam lithography allows the effects relating to light diffraction during etching of nanometric devices to be disregarded.

Figure 8D:
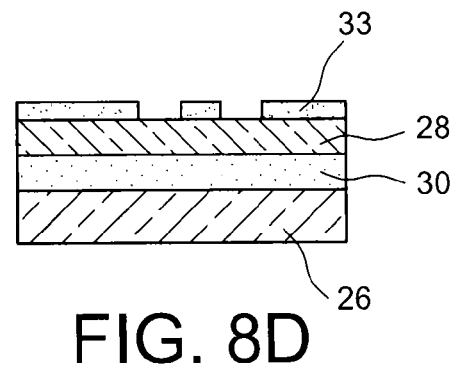

The element formed in this manner is represented in FIG. 8D.

In a subsequent step, the silicon layer is etched, for example by anisotropic Reactive Ion Etching (RIE).

Figure 8E:
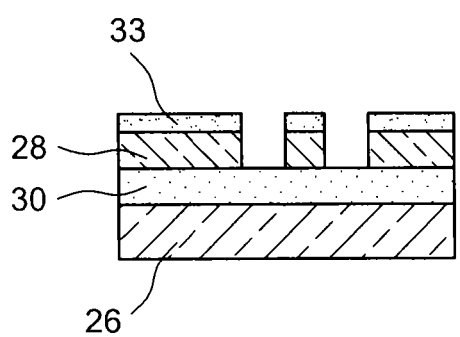

The element formed in this manner is represented in FIG. 8E.

In a subsequent step, a chemical deposition of $SiO_2$ 34 is made on etched silicon layer 28, which is then etched, for example by plasma etching, to delimit positions 36 of the electrical contacts.

Electrical contacts 38 are then made by depositing, for example, aluminium, for example by spray deposition.

Figure 8F:
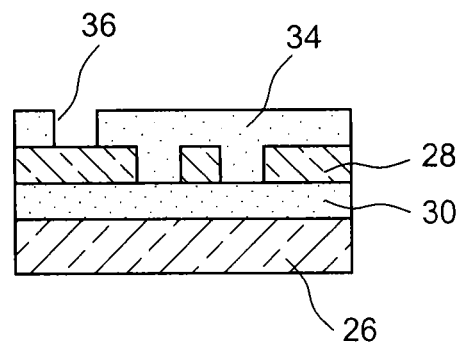
Figure 8G:
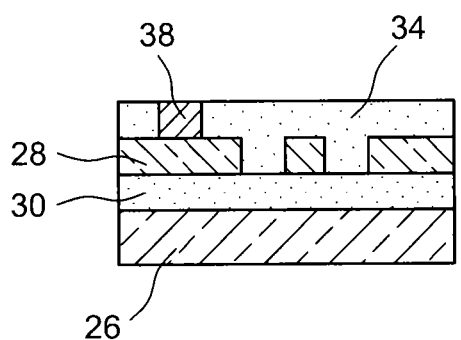
Figure 8H:
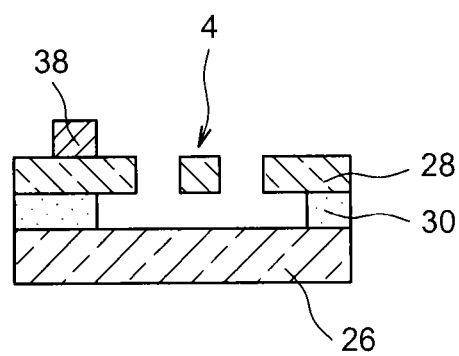

The element obtained in this manner is represented in FIG. 8F.

In a subsequent step, the structure is released, for example by etching layer 30, for example with hydrofluoric acid vapour.

The released structure can be seen in FIG. 8F. Membrane 4 and the nanowires are thus produced as a single part made of monocrystalline silicon.

As an example, layer 28 is 160 nm thick, buried oxide layer is 400 nm thick, silicon layer 26 is 750 μm thick, oxide layer 32 is 400 nm thick and resin layer 33 is 800 nm thick.

In the case of the oxide and the resin these values are orders of magnitude; depending on the desired resolution they may vary, but are less, or preferably less, than one micron.

A heat flux sensor has thus been produced which has sensitivity to changes of composition of the gaseous environment. In addition its small dimensions make it very compact.

The heat flux sensor is particularly suitable for production of a gas sensor. Such a gas sensor may advantageously be associated with a gas chromatography column, and more specifically with a gas chromatography microcolumn. A gas analysis device may comprise a gas chromatography microcolumn and a sensor according to the invention positioned in a channel connected in series with the outlet of the microcolumn, and an electronic unit for processing the signals delivered by the sensor.

The microcolumn is advantageously made using microelectronics techniques.

The analysis device preferably comprises several sensors in series.

The analysis device may comprise several microcolumns, where each is connected in series directly with a sensor according to the invention, and by this means forming a subassembly. The device then comprises multiple subassemblies connected in series. The electronic processing unit is advantageously common to all the sensors.

The gaseous blend to be analysed is injected in the microcolumn, and the different analytes are then separated, leaving the column in succession. The sensor or sensors then detect analyte peaks which are staggered over time.

This measuring device is very compact and has a very satisfactory resolution.

The invention claimed is:

1. A heat flux sensor comprising:
   at least one first support;
   at least one first membrane being suspended relative to the first support by a set of at least four nanowires providing mechanical suspensions connecting from the at least one first membrane to the first support;
   said first membrane being made from at least one current-conducting material;
   the at least four nanowires being made from a current-conducting material;
   two nanowires of the set of at least four nanowires connected respectively between 1) one of two terminals on the first support and 2) the at least one first membrane, the two terminals capable of providing a current from a current source to polarise the first membrane and said two nanowires acting as a heater for heating said first membrane; and
   at least two nanowires of the set of at least four nanowires being connected to a device for measuring the voltage at the terminals of the first membrane.

2. A heat flux sensor according to claim 1, in which the nanowires have a section of between 10×10 nm² and 1000×1000 nm².

3. A heat flux sensor according to claim 1, in which the first membrane is between 10 nm and 1 µm thick.

4. A heat flux sensor according to claim 1, in which the first membrane and the nanowires are formed by the same current-conducting material such that the first membrane and the nanowires form a single piece.

5. A heat flux sensor according to claim 4, in which the first membrane and the nanowires are made of a semiconductor material.

6. A heat flux sensor according to claim 4, in which the first membrane and the nanowires are made of N- or P-doped silicon, germanium or SiGe.

7. A heat flux sensor according to claim 1, in which the first membrane comprises a first portion forming a single part with the nanowires, and a second portion formed by a layer of material formed on the first portion, the material of the nanowires and the first portion having low thermal conductivity, and the material of the second portion has a high temperature coefficient of resistance.

8. A heat flux sensor according to claim 7, in which the thermal conductivity of the material of the nanowires and of the first portion is less than 100 W/m·K and the temperature coefficient of resistance of the material of the second portion is greater than 1000 ppm/K.

9. A heat flux sensor according to claim 7, in which the nanowires and the first portion are made of silicon and the second portion is made of TiN.

10. A heat flux sensor according to claim 1, in which the current source is an alternating current source.

11. A heat flux sensor according to claim 10, in which the alternating current source has a frequency of between 10 Hz and 1 MHz.

12. A heat flux sensor according to claim 10, in which the alternating current source has a frequency of between 1 kHz and 10 kHz.

13. A heat flux sensor according to claim 1, comprising additional suspension elements configured solely for mechanical suspension of the first membrane relative to the support.

14. A heat flux sensor according to claim 1, comprising embedments of the nanowires and/or of additional suspension elements on the support, wherein the embedments of the nanowires and/or of the additional suspension elements are nano-structured so as to reduce the thermal conduction of the embedments.

15. A heat flux sensor according to claim 1, in which the first membrane has the shape of a rhomb, and in which the nanowires are connected to the apexes linked by the larger diagonal of the rhomb.

16. A heat flux sensor according to claim 1, comprising a second membrane suspended from a second support by said set of at least four nanowires, said second membrane being positioned parallel to the first membrane at a non-zero distance, and said two nanowires of said set being connected to a second current source to polarise the second membrane between two terminals, and said at least two nanowires of said set being connected from the voltage measurement device to the terminals of the second membrane.

17. A heat flux sensor according to claim 16, in which the first and second current sources are alternating current sources, and the second current source delivers a current of a frequency different to the frequency of the current delivered by the first current source.

18. A heat flux sensor according to claim 17, in which the first and second current sources are direct current sources, and the second current source delivers a current which is lower than the current delivered by the first current source, so as to prevent self-heating in the second membrane.

19. A system for determining the concentration of a gaseous environment comprising:
   at least one heat flux sensor according to claim 1; and
   an electronic unit for processing the electrical voltage values delivered by the sensor.

20. A device for analysing a gas or a blend of gases comprising:
   a gas chromatography column (CG); and
   at least one determination system according to claim 19, wherein
   the membrane is suspended in a channel connected to the outlet of the gas chromatography column.

* * * * *